US007048767B2

(12) United States Patent
Namavar

(10) Patent No.: US 7,048,767 B2
(45) Date of Patent: May 23, 2006

(54) NANO-CRYSTALLINE, HOMO-METALLIC, PROTECTIVE COATINGS

(75) Inventor: Fereydoon Namavar, Westford, MA (US)

(73) Assignee: Spire Corporation, Bedford, MA (US)

( * ) Notice: Subject to any disclaimer, the term of this patent is extended or adjusted under 35 U.S.C. 154(b) by 34 days.

(21) Appl. No.: 10/166,798

(22) Filed: Jun. 11, 2002

(65) Prior Publication Data

US 2003/0229399 A1    Dec. 11, 2003

(51) Int. Cl.
*A61F 2/28* (2006.01)
(52) U.S. Cl. .................. 623/23.6; 623/23.53; 427/2.24
(58) Field of Classification Search ............. 623/23.53, 623/23.6; 427/450, 452–456
See application file for complete search history.

(56) References Cited

U.S. PATENT DOCUMENTS

| | | | |
|---|---|---|---|
| 5,004,476 A | 4/1991 | Cook | |
| 5,180,394 A | 1/1993 | Davidson | |
| 5,236,509 A | 8/1993 | Sioshansi et al. | |
| 5,370,694 A | 12/1994 | Davidson | |
| 5,489,306 A | 2/1996 | Gorski | |
| 5,702,448 A | 12/1997 | Buechel et al. | |
| 5,861,042 A | 1/1999 | Buechel et al. | |
| 5,865,850 A | 2/1999 | Matthews | |
| 5,955,145 A | 9/1999 | Kalvala et al. | |
| 5,981,827 A | 11/1999 | Devlin et al. | |
| 6,051,751 A | 4/2000 | Sioshansi et al. | |
| 2002/0042656 A1 | 4/2002 | Hunter et al. | |

FOREIGN PATENT DOCUMENTS

EP    0 461 032    12/1991
FR    2 789 315    8/2000

OTHER PUBLICATIONS

Savader, et al. "*Nanoidentation Study of Sputtered Nanocrystalline Iron Thin Films*"Scripta Materialia, vol. 36, No. 1, pp. 29-34 (1997).
Lavemia, et al. "*The Corrosion Properties of Nanocrystalline CO-CR Coatings*" 48th Annual Meeting of the Orthopaedic Research Society, paper No. 0162.
Lau, et al., "Synthesis and Characterization of Nanocrystalline Co-CR Coatings by Plasma Spraying" Nanostructured Materials, Elsevier, New York, NY, US (Jul. 1998).

*Primary Examiner*—Thomas C. Barrett
(74) *Attorney, Agent, or Firm*—Thomas J. Engellenner; Reza Mollaaghababa; Nutter McClennen & Fish LLP

(57) ABSTRACT

The present invention provides orthopedic prosthesis having at least one metallic component that includes a metallic substrate on which an integrally formed nano-crystalline coating is formed. The coating and the substrate have at least one metallic constituent in common having an average atomic concentration in the coating that differs from an average atomic concentration in the substrate by less than about 10 percent. Further, the nano-crystalline coatings includes crystalline grains with an average size in a range of about 1 to 999 nanometers, and more preferably in a range of about 10 to 200 nanometers. A transition region that exhibits a graded reduction in average grain size separates the coating from the substrate. The coating advantageously exhibits an enhanced hardness, and a high degree of resistance to corrosion and wear. In one application, the nano-crystalline coatings of the invention are utilized to form articulating surfaces of various orthopedic devices.

59 Claims, 5 Drawing Sheets

(NOT TO SCALE)

NANO-CRYSTALLINE, HOMO-METALLIC, PROTECTIVE COATINGS

BACKGROUND

The present invention relates generally to metallic structures having protective coatings and methods for producing such structures. More particularly, the invention provides metallic components for incorporation in orthopedic prosthesis which include surfaces having integrally formed protective coatings that exhibit a high degree of hardness, wear and corrosion resistance.

Metallic structures are utilized in a variety of devices. For example, many prosthetic devices include metallic components. In particular, prosthetic joints, utilized in total joint arthroplasty (TJA) procedures to restore mobility in patients with reduced joint function, typically include two mating and articulating surfaces, one of which is formed of a metal alloy such as titanium-aluminum-vanadium or cobalt-chromium-molybdenum, and the other is formed and/or lined with a plastic component, such as ultrahigh molecular weight polyethylene (UHMWPE).

The recent trends in performing arthroplasty on younger and more active patients have increased the demand for enhanced prosthetic joint function and lifetime. The lifetime of total joint replacement components is typically limited either by gross failure of the materials of the articulating surfaces (primarily the UHMWPE component) or by biological reactions to debris generated from the wear of the articulating surfaces. UHMWPE wear particles have been implicated as a major contributing factor to bone resorption, joint loosening, and osteolysis, necessitating replacement of the prosthetic components. In addition, wear debris can result in the formation of scar tissue which, in turn, can lead to decreased joint mobility and pain. For example, wear of the UHMWPE acetabular component in artificial hips has been measured to be between 0.02 and 0.25 mm/year, with an average wear rate of about 0.07 mm/year.

A number of mechanisms can contribute to the rate of the wear of UHMWPE articulating surfaces. One such mechanism is abrasive wear which is caused primarily by surface asperities on a hard metallic or ceramic surface in contact with the UHMWPE articulating surface. Further, wear particles, such as metallic and ceramic particles, corrosion products, and bone fragments can migrate to the joint capsule and accumulate at bone prosthesis interface. These third body wear particles, produced primarily from components of bone cement used to secure the joints, produce a wear environment that facilitates roughening of the metallic surfaces.

One suggested approach for lowering the wear rate of UHMWPE components in such prosthetic devices is to coat the metallic mating surfaces with hard ceramics. However, such ceramic coatings have a number of drawbacks. For example, it is difficult to achieve adequate adhesion between the metal and the ceramic. Further, such ceramic coatings are brittle and can render manufacturing of the prosthetic devices which utilize them difficult and costly.

Thus, a need exists for protective coatings on metallic surfaces that can enhance the hardness, and the wear and corrosion resistance of such surfaces. Further, a need exists for metallic components in prosthetic devices which exhibit a high degree of wear and corrosion resistance. In addition, a need exists for methods of manufacturing such coatings which are easy to implement and are also cost effective.

SUMMARY OF THE INVENTION

The present invention provides, nano-crystalline, homo-metallic coatings having average grain sizes in a range of about 1 to about 999 nanometers. The term "homo-metallic coating", as used herein, refers to a coating, formed on a metallic substrate, which has at least one metallic constituent element in common with the metallic substrate. For example, when the substrate is formed of a Co—Cr—Mo alloy, a homo-metallic coating can be formed of a Co—Cr alloy, a Co—Cr—Mo alloy, a Cr—Mo alloy, a Co—Mo alloy, chromium, cobalt, or molybdenum.

In one aspect, the present invention provides an orthopedic prosthesis for implantation in a patient that includes at least one metallic component formed of a metallic substrate having a homo-metallic protective coating integrally formed thereon. The coating and the substrate have at least one metallic constituent in common. The average atomic concentration of the common metallic constituent in the coating differs from its average concentration in the substrate by less than about 20 percent, and more preferably, by less than about 10 percent. Further, the protective coating has a nano-crystalline structure with average grain sizes ranging from about 1 nanometer to about 999 nanometers, and preferably from about 1 nanometer to about 500 nanometers, and more preferably from about 10 nanometers to about 200 nanometers. A transition region that exhibits a graded reduction in average grain size of the common metallic constituent separates the coating from the substrate. For example, the average crystalline grain size can decrease continuously from the substrate to the coating within the transition zone. Such a transition zone can advantageously enhance the adhesion of the coating to the substrate.

The common metallic constituent can be, for example, cobalt having an average atomic concentration in a range of about 40 to about 75 percent, and preferably in a range of about 45 to about 65 percent, and more preferably, in a range of about 50 to about 60 percent. Further, the substrate and the coating can include more than one common metallic constituents. For example, in addition to cobalt, the substrate and the coating can both include chromium (Cr) at an average atomic concentration in the substrate in a range of about 30 to about 65 percent, and preferably, in a range of about 35 to about 55 percent, and more preferably in a range of about 40 to about 50 percent, and an average atomic concentration in the coating which differs from that in the substrate by less than about 20 percent, and more preferably, by less than about 10 percent.

Alternatively, the common metallic constituent can be titanium (Ti). For example, the substrate and the coating can be formed of a Ti-6Al-4V alloy. In yet another example, a nano-crystalline coating of stainless steel can be deposited on a stainless steel substrate.

The substrate and/or the coating can also include other metallic elements. For example, the substrate can include molebdynum (Mo) as one of its constituents. In particular, in one embodiment, the substrate includes a $Co_{57.1}Cr_{37.2}Mo_{5.7}$ alloy and the nano-crystalline coating includes a $Co_{60.5}Cr_{39.5}$ alloy. It should also be understood that the substrate and/or the nanocrystalline coating can include non-metallic elements, such as nitrogen. The concentration of such a non-metallic element can be, for example, less than about 20 percent, and more preferably, less than about 10 percent.

According to other aspects, the protective coating can have a thickness ranging from about 0.05 microns to about a few millimeters. Alternatively, the thickness of the coating can range from about 0.05 microns to about 10 microns, or from about 0.3 microns to about 3 microns.

A "nanocrystalline coating" according to the invention typically will have an average crystalline grain size that is approximately 100 times to 400 times less than the average crystalline grain size of the underlying substrate. Accordingly, a nano-crystalline coating of the invention advantageously generally exhibits substantially greater hardness than that of the underlying substrate. For example, the hardness of the protective coating of the invention can be about 10%, and more preferably 30%, greater than that of the substrate. The hardness of a nano-crystalline coating of the invention typically will be in a range of approximately 10 to about 30 GPa.

In another aspect, an orthopedic prosthesis according to the teachings of the invention can include a plastic component that can articulate against the metallic component, which is at least partially coated with a homo-metallic coating according to the teachings of the invention. The plastic component can be formed of a variety of materials known in the art. For example, the plastic component can be formed or lined with ultra-high molecular weight polyethylene (UHMWPE). The prosthesis can be, for example, an artificial hip, an artificial knee, or an artificial shoulder.

In another aspect, a transition region separating a homo-metallic nano-crystalline coating of the invention from the substrate on which the coating is deposited is characterized by a graded variation of concentration of the common metallic constituent from the protective coating to the substrate.

In another aspect, the invention provides methods for producing a protective coating on a metallic surface of a metallic component of an orthopedic prosthesis. One such method calls for depositing a dose of a metallic substance on a metallic substrate, where the deposited substance and the substrate have at least one metallic constituent element in common. The deposition step can be performed, for example, by evaporating the metallic substance and depositing the evaporated atoms onto the substrate.

Concurrent with the deposition step, the metallic surface is bombarded with one or more selected ions so as to form a nano-crystalline integral protective coating on the surface, having average grain sizes ranging from about 1 nm to about 999 nm, and having an average atomic concentration of the common constituent element that differs from its average concentration in the metallic surface by less than about 20 percent, and more preferably, by less than about 10 percent. An ion beam, e.g., argon or nitrogen or a mixture of argon and nitrogen, can be directed onto the substrate to assist in the formation of the integral coating.

The ion beam incident on the substrate can have a current density in a range between about 1 to about 500 microamperes per square centimeters ($\mu A/cm^2$). Further, the energy of the ion beam can be selected to be in a range of about 0.05 keV to about 10 keV, and more preferably, from about 0.1 keV to about 2 keV. Further, the deposition rate of the metallic substance over the substrate can be in a range of about 0.1 to about 1000 angstroms per second (Å/sec), preferably from about 0.1 to about 100 angstroms per second, and more preferably, from about 0.5 to about 50 angstroms per second.

In another aspect, the metallic surface can be selected to be any of a Co—Cr, Co—Cr—Mo, or a titanium alloy.

Moreover, the deposition and ion bombardment steps can be performed while the substrate is maintained at a variety of different temperatures. For example, in one embodiment, no heating or cooling provisions are provided for stabilizing the temperature of the substrate. In such an embodiment, the deposition and ion bombardment steps resume while the substrate is at room temperature. These processes can, however, raise the substrate temperature above its initial value.

In another aspect, the invention provides methods as described above in which the deposition rate of the metallic substance and the current density of the incident ion beam are selected such that a ratio of the substance atoms deposited on the substrate per second relative to the number of ions incident on the substrate per second is in a range of about 1 to about 10.

Illustrative embodiments of the invention are described below with reference to the following drawings.

DETAILED DESCRIPTION

The present invention provides metallic structures having integrally formed, homo-metallic, protective coatings with nano-crystalline structures. The nano-crystalline structures of the coatings include crystalline grains with mean sizes in a range of about 1 nanometers to about 999 nanometers. More preferably, the average crystalline grain sizes of the coatings are in a range of about 10 to 200 nanometers. The nano-crystalline coatings of the invention advantageously exhibit a high degree of hardness, and enhanced wear and corrosion resistance properties.

Figure 1:
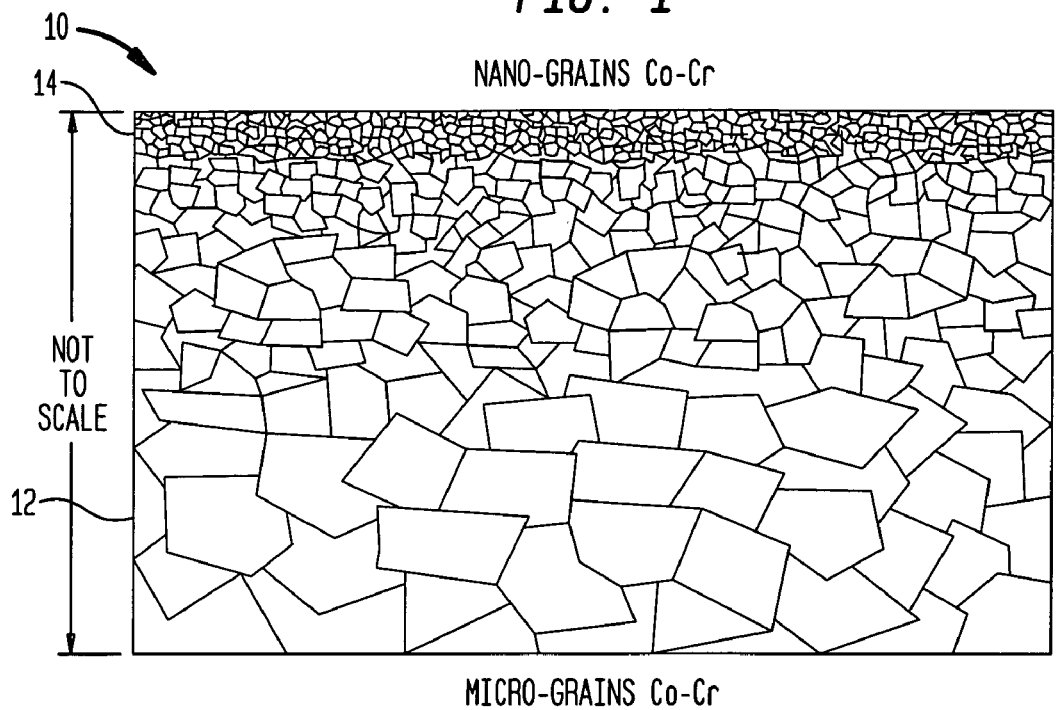
FIG. 1 schematically illustrates a graded nano-crystalline homometallic Co—Cr alloy coating deposited on a microcrystalline Co—Cr prosthesis surface in accordance with the teachings of the invention.

FIG. 1 schematically illustrates a metallic structure 10 formed in accord with the teachings of the invention that can form at least a portion of a metallic component of an orthopedic prosthesis of the invention. The metallic structure 10 includes a cobalt-chromium (Co—Cr) substrate 12 and a Co—Cr nano-crystalline coating 14. The substrate 12 includes a plurality of micron-sized crystalline grains. In contrast, the coating 14 includes crystalline grains with sizes that are approximately 100 to 400 times smaller than those of the substrate 12. More specifically, the average grain sizes of the coating 14 can be in a range of about 1 to about 999 nanometers.

A nano-crystalline coating of the invention, such as the coating 14 above, can have a thickness in a range of about 0.1 microns to a few millimeters. More preferably, the thickness of the nano-crystalline coating is in a range of approximately 0.5 to 3.0 microns. The coating and the substrate can have a non-discrete (graded) interface boundary. That is, a transition zone, having crystalline grain sizes with values intermediate those of the coating and the substrate, can separate the coating from the bulk substrate.

In one aspect, the invention provides metallic structures that exhibit a gradual reduction of crystalline grain size from a homo-metallic coating layer to the bulk substrate. Such a gradual reduction of the grain size advantageously ensures an enhanced adhesion of the coating layer with the remainder of the structure. Further, the nano-crystalline grain structure of the coating provides superior hardness compared with corresponding materials having larger crystalline grain sizes, thus enhancing the durability of the coating.

The coating films, e.g., homometallic coatings, of the invention provide a number of distinct advantages. For example, corrosion studies performed on Co—Cr coatings formed on Co—Cr—Mo substrates in accord with the teachings of the invention (See Example 1 below) indicate that such coatings exhibit at least one order of magnitude increase in corrosion resistance compared with the bulk material. Further, nano-crystalline coatings of the invention exhibit a high degree of hardness, e.g., in a range of about 10 to 30 GPa. For example, nano-crystalline Co—Cr coatings formed on Co—Cr—Mo substrates in accordance with the teachings of the invention exhibit hardness close to those of some ceramics, such as TiN, CrN, $Al_2O_3$ and $Zr_2O_3$, without having the associated problems of adhesion to metal substrates.

Figure 2:
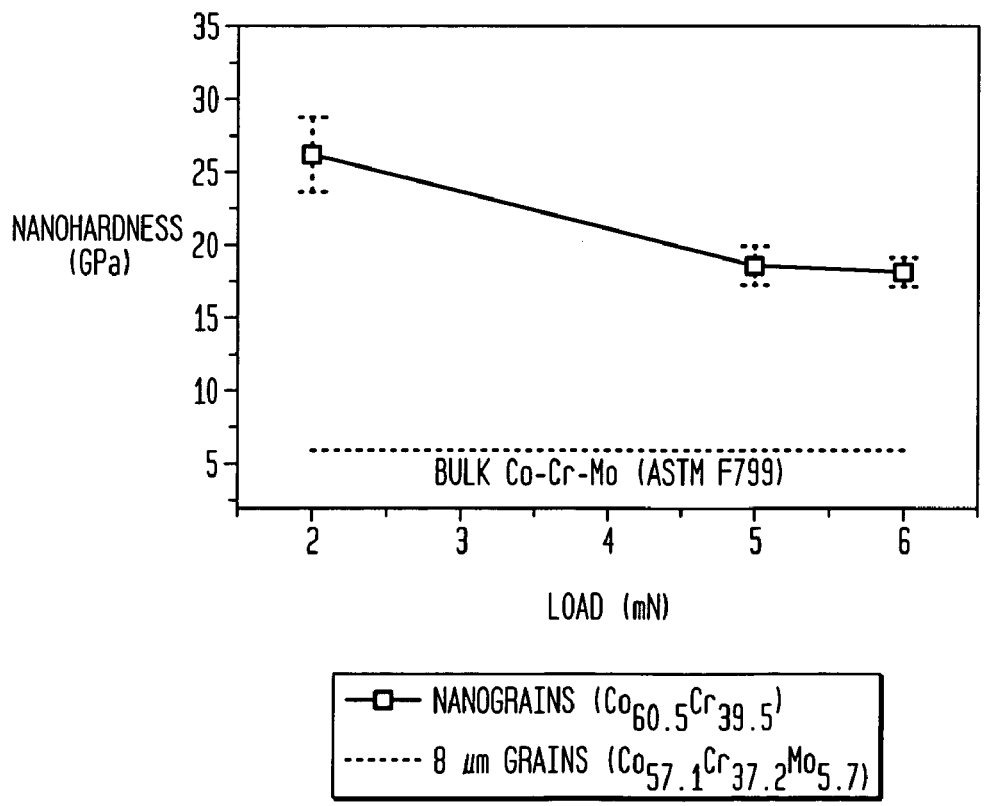
FIG. 2 is a diagram illustrating measured nano-hardness of a Co—Cr nano-crystalline coating and its comparison with the nano-hardness of a Co—Cr—Mo substrate on which the coating can be deposited.

FIG. 2 presents a comparison of nano-indentation measurements for a Co—Cr nano-crystalline coating deposited on a Co—Cr—Mo substrate in accord with the teachings of the invention. The measurement of the coating hardness was conducted by utilizing an ultramicro-indentation system which employs a sharp Berkovich diamond (three-sided diamond) indenter with a minimum force of 0.1 mN. The maximum load was adjusted such that the maximum penetration depth corresponded to less than 10–15% of the coating thickness to minimize the influence of the substrate on the measurements. Further, the applied force was incremented in 30 steps in a square root progression until the maximum load was achieved. This was followed by a hold segment of about 100 seconds to allow for relaxation of induced plastic flow and creep. Finally, the unloading segment was measured by decreasing the force. The measurements indicate that the nano-crystalline coating exhibits a substantial increase in hardness relative to that of the bulk substrate.

Figure 3:
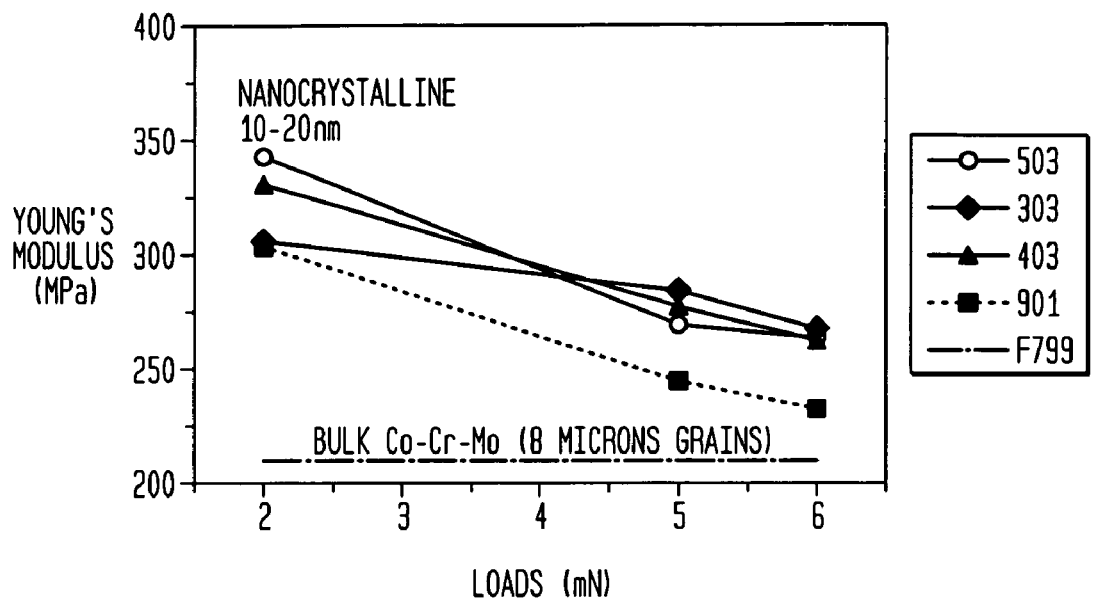
FIG. 3 presents a comparison of the measured Young's moduli for a plurality of nano-crystalline Co—Cr coatings with the Young's modulus of a Co—Cr—Mo substrate on which the coatings are deposited.

FIG. 3 presents measurements of the Young's modulus for a number of homo-metallic nano-crystalline coatings. An inspection of the graphs of FIG. 3 illustrates that the Young's moduli of these nano-crystalline coatings are advantageously much larger than the Young's modulus of the substrate, attesting to the enhanced hardness of such coatings.

Figure 4:
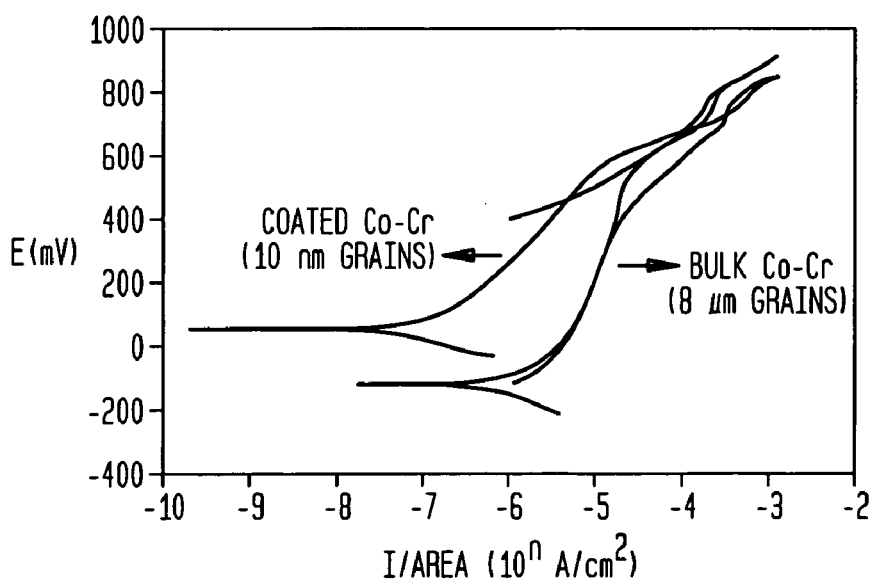
FIG. 4 presents a comparison of the potentiodynamic data for a nano-crystalline Co—Cr film in accord with the teachings of the invention with the data for a Co—Cr—Mo bulk substrate illustrating significantly improved static corrosion behavior of the nano-crystalline coating.

The nano-crystalline coatings of the invention also exhibit a substantial increase in corrosion resistance relative to the bulk substrate material. For example, FIG. 4 presents a comparison of the potentiodynamic polarization data for a Co—Cr film of the invention having crystalline grains with an average size of about 10 nm with data for a Co—Cr—Mo bulk substrate having crystalline grains with an average size of about 8 microns on which the Co—Cr film is deposited. This comparison illustrates that the Co—Cr nano-crystalline coatings of the invention exhibit significantly improved static corrosion behavior relative to the wrought Co—Cr—Mo alloy samples.

A number of techniques can be utilized to form homometallic nano-crystalline coatings, such as those described above. For example, one embodiment of the invention generates integrally formed nano-crystalline homo-metallic coatings on metallic substrates by utilizing an ion beam assisted deposition (IBAD) process. In particular, physical vapor deposition combined with concurrent ion beam bombardment can be utilized to produce a wide variety of nano-crystalline homo-metallic coatings in accord with the teachings of the invention.

Figure 5:
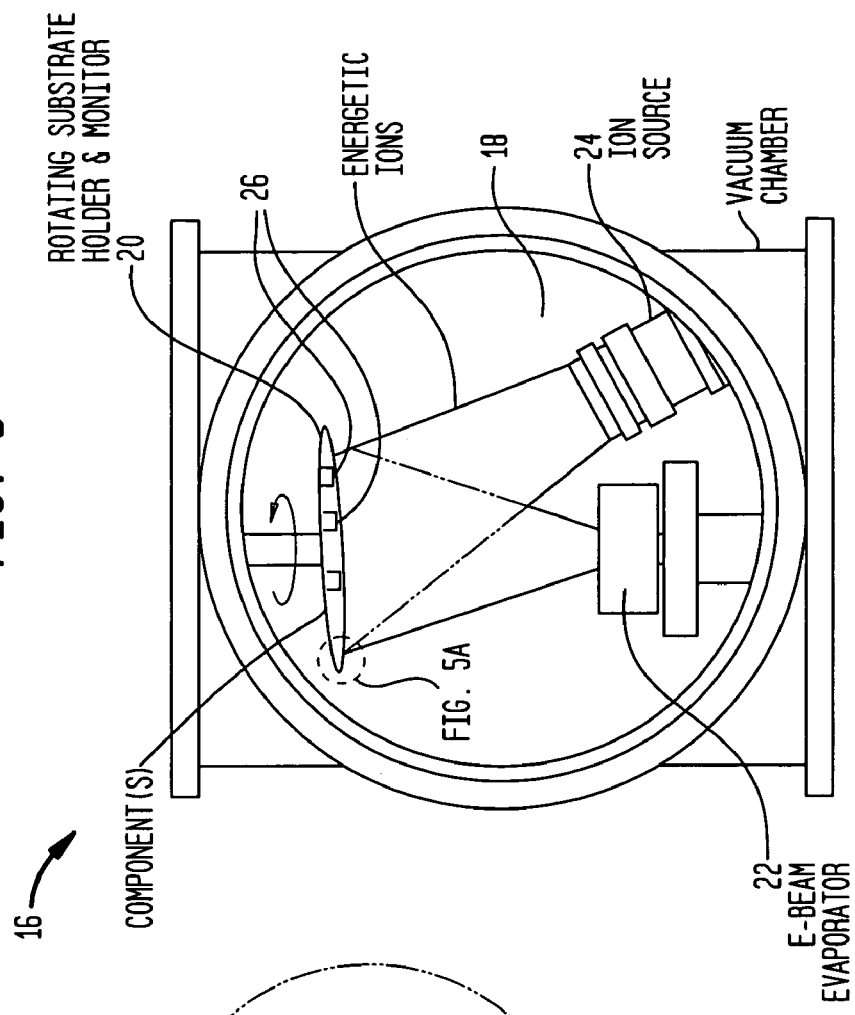
FIG. 5 is a schematic illustration of an IBAD apparatus suitable for producing homo-metallic nano-crystalline coatings in accord with the teachings of the invention.
Figure 5A:
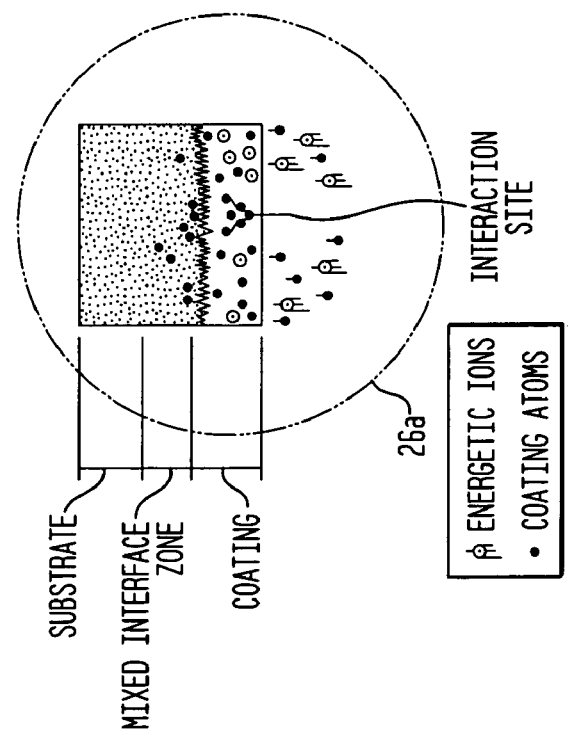

FIG. 5 schematically illustrates an IBAD system 16 that is suitable for the practicing the invention. Such IBAD systems are known in the art. For example, U.S. Pat. No. 5,236,509, herein incorporated by reference, describes an IBAD apparatus that is suitable for use in producing homo-metallic nano-crystalline coatings in accord with the teachings of the invention.

The exemplary IBAD system 16 includes a vacuum chamber 18 in which a substrate holder 20, an electron beam evaporator 22, and an ion source 24 are placed. A base pressure less than about $10^{-6}$ torr and an operating pressure of approximately $10^{-5}$ torr are typically maintained in the chamber 18. The holder 20 permits positioning a plurality of substrates 26 in the chamber 18 for subsequent processing, as discussed below.

The processing of each substrate 26, which results in creation of an integral coating having a nano-crystalline structure, can be perhaps better understood by considering one of these substrates, i.e., substrate 26a, shown in the insert of FIG. 5. The substrate 26a is exposed to a vapor flux of atoms of a selected material, e.g., a metal such as Co or Cr or an alloy such as Co—Cr, or stainless steel, generated by the electron beam evaporator 22 to grow a film of the selected material over the substrate.

Concurrent with the vapor deposition, the growing film is bombarded with ions of a selected gas, e.g., argon, generated by the ion source 24. The ion energies are selected to be in a range of about several hundred to several thousand electron volts (eV), e.g., in a range of approximately 500 eV to approximately 2000 eV. More preferably, the ion energies lie in a range of about 500 eV to about 1000 eV. The current density of the ion beam ranges from about 50 microamperes per square centimeter ($\mu A/cm^2$) to about 300 microamperes per square centimeter ($\mu A/cm^2$).

In general, the IBAD process includes a number of parameters, each of which can influence the properties of the coating film generated on a substrate surface. Some of these parameters include deposition rate, ion species, ion energy and ion beam current density. Metal evaporation rates utilized to create integral metal coatings in accord with the invention can vary from about 2 angstroms per second (Å/s) to approximately 50 (Å/s). More preferably, the deposition rate is selected to be in a range of about 2 angstroms per second (Å/s) to about 20 Å/s to ensure that the ion bombardment is effective in modulating the properties of the growing film. The current density of the ion beam bombarding the substrate can be in a range between about 50 to about 200 microamperes per square centimeter. Moreover, the energy of the ion beam can be selected to be in a range of about 0.5 keV to about 1 keV.

One embodiment of the invention preferably utilizes argon ions for bombardment of the substrate. Argon is an inert gas, and hence does not create potential complications associated with the presence of a reactive element in the alloy coating. Alternatively, nitrogen ions or a mixture of argon and nitrogen ions can be utilized for bombarding the substrate.

The IBAD process can be performed while the substrate is maintained at any desired temperature. In some embodiments of the invention, no provision is provided for raising the substrate temperature above a value determined by the ambient temperature and the impact of atoms and ions on the substrate. In other embodiments, the substrate temperature is raised to a higher value, e.g., 400° C. In yet other embodiments, the substrate temperature can be modulated during the simultaneous evaporation and bombardment to create a gradient of crystalline grain size in a homo-metallic film deposited on the substrate.

Other techniques for producing homo-metallic coatings in accord with the teachings of the invention include, but are not limited to, sputtering, plasma immersion, and laser ablation.

The methods of the invention can be utilized to form nano-crystalline coatings on metallic structures having a variety of geometrical shapes. For example, spherical metallic components having homometallic coatings with nano-crystalline grains can be produced in accord with the teachings of the invention.

The metallic structures of the invention having homometallic nano-crystalline coatings can find a variety of applications. For example, such metallic structures can form components of various orthopedic devices, such as hip joints, knee joints, and elbows. Such orthopedic applications of metallic structures of the invention provide a number of advantages. For example, the use of superhard, nano-crystalline coatings significantly ameliorates the generation of wear debris at the articulating interface, thereby providing increased UHMWPE longevity and decreased osteolytic response. Other benefits can include, for example, a reduction of polyethylene wear associated with scratched metal prostheses, reduction of backside wear in tibial trays and rotating and sliding meniscal bearing tibial components.

Figure 6A:
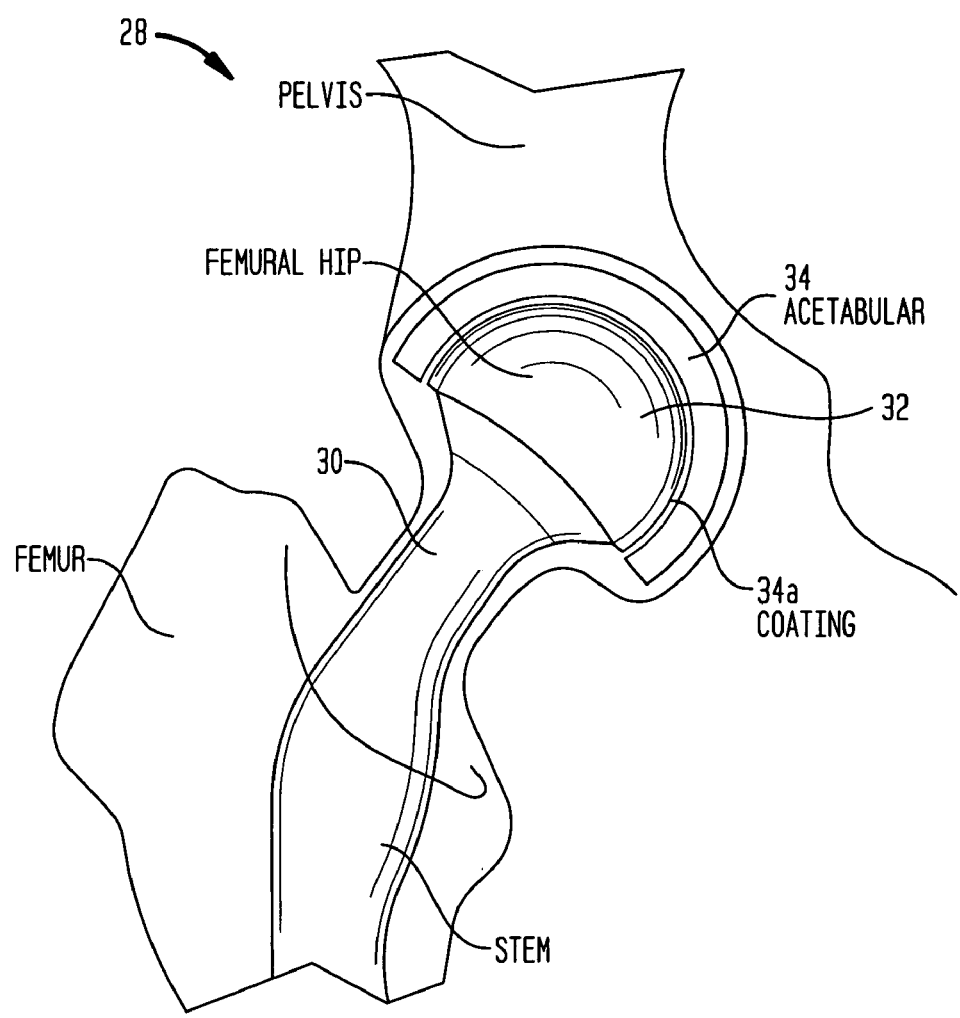
FIG. 6A is a schematic illustration of a hip joint prosthesis that includes a metallic femoral head having a metallic surface coated according to the teachings of the invention articulating against the surface of a cup lined with UHM-WPE, FIG. 6B schematically illustrates coated surface of the cup in hip joint prosthesis of FIG. 6A against which the femoral head articulates, FIG. 7 schematically illustrates a knee joint prosthesis having an articulating surface formed as a nano-crystalline homo-metallic film in accord with the teachings of the invention.
Figure 6B:
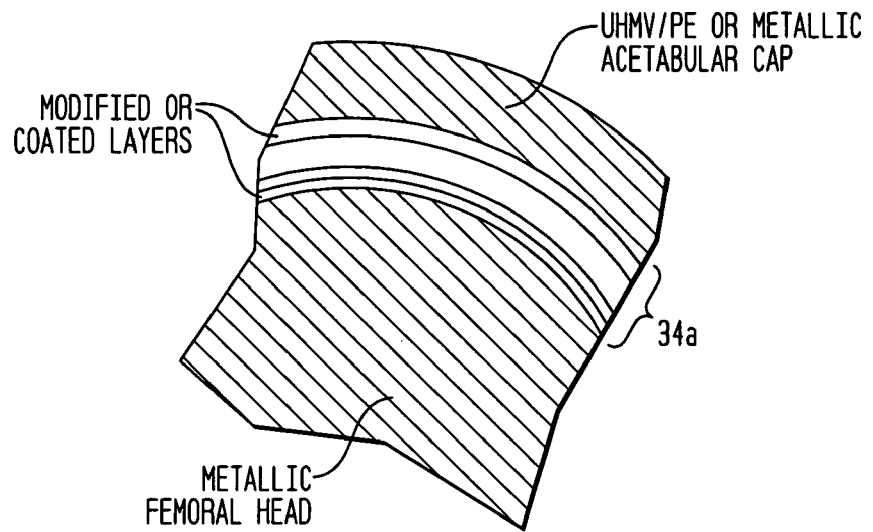

By way of example, FIG. 6A illustrates a typical hip joint prosthesis 28 having a stem 30, which fits into the femur, a femoral head 32, and an acetabular cup 34 against which the femoral head articulates. As shown schematically in FIG. 6B, the acetabular cup 34 can be lined with one or more layers 34a formed of an organic polymer or polymer composites. For example, ultra-high molecular weight polyethylene (UHMWPE) can be utilized to provide a polymer lining on an articulating surface 34a of the acetabular cup 34. The femoral head 32 can be formed of a metallic component in accord with the teachings of the invention having a metallic substrate on which a protective coating with a nano-crystalline structure is integrally formed. For example, the femoral head can be formed of a Co—Cr—Mo alloy having a Co—Cr nano-crystalline coating in the accord with the teachings of the invention.

Figure 7:
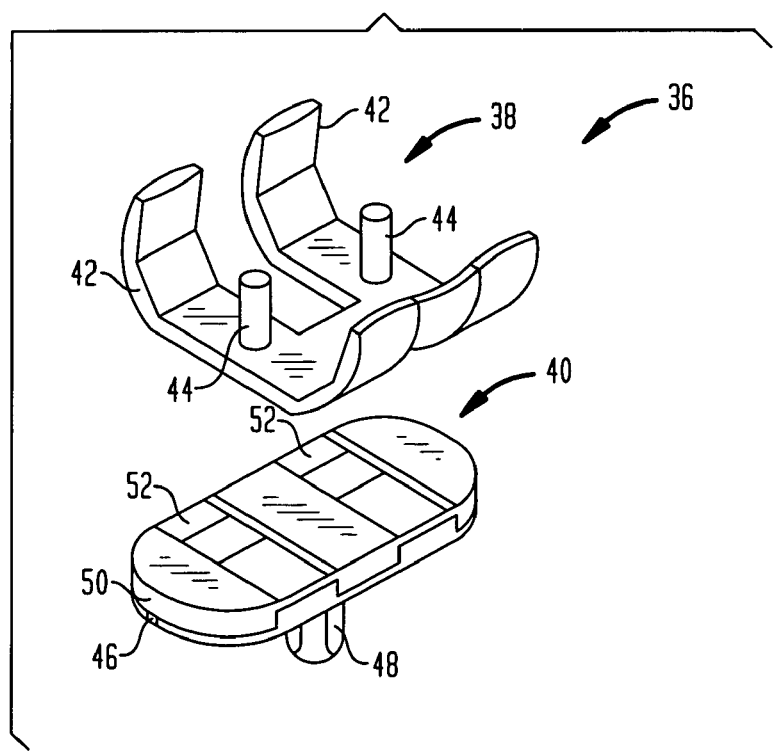

As another example of the use of homometallic nano-crystalline coatings of the invention, FIG. 7 schematically depicts a knee joint prosthesis 36 having a femoral component 38 and a tibial component 40. The femoral component 38 includes condyles 42 which provide the articulating surface of the femoral component and pegs 44 that allow attachment of the femoral component to the femur. The tibial component 40 includes a tibial base 46 with a peg 48 that allows mounting the tibial base onto the tibia. The tibial component 40 further includes a platform 50, mounted on the base 46, and having grooves 52 with a shape similar to that of the condyles 42. The condyles 42 articulate within the grooves 52 against the tibial platform 48. The tibial platform can be formed of and/or lined with an organic polymer, such as UHMWPE. The condyles 42 can be formed of metallic structures according to the invention. In particular, the condyle surfaces articulating within the grooves 52 can be formed of homometallic nano-crystalline films in accord with the teachings of the invention.

Those skilled in the art will appreciate that various modifications can be made to the above embodiments without departing from the scope of the invention. For example, the metallic substrates on which nano-crystalline homo-metallic coatings in accord with the teachings of the invention can be formed are not limited to those described above. Moreover, the applications of homo-metallic coatings of the invention are not limited to orthopedic devices.

The following example provides further illustration of the invention including exemplary methods for generating nano-crystalline homo-metallic coatings on metallic substrates. This examples is provided only for illustrative purposes, and is not intended to be limiting of the scope of the invention.

EXAMPLE 1

A plurality of nano-crystalline coatings of Co—Cr was formed on a Co—Cr—Mo substrate (F799 substrate) having an average chemical composition of $Co_{57.12}Cr_{37.2}Mo_{5.7}$. The chemical composition of the substrate was determined by utilizing Rutherford Backscattering Spectrometry.

To produce these films, a Co—Cr alloy was evaporated and the evaporated atoms were directed to the surface of the substrate. Concurrently, the substrate was bombarded with a beam of argon ions, having a current density in a range of about 50 to 150 microamperes per square centimeter ($\mu A/cm^2$) and an ion energy of 500 or 600 eV. The process of simultaneous deposition and ion bombardment of the substrate continued for a selected time period to produce a nano-crystalline film having a desired thickness.

TEM studies of these Co—Cr coatings show that the grain sizes of the coatings range from about 20 nm to about 40 nm. That is, the coatings include grains having sizes that are a few hundred times smaller than those of the bulk substrate. Further, these studies show that the nano-crystalline coatings are substantially free of dislocations. Moreover, electron diffraction pattern obtained from a 2-micron area of this coating showed a plurality of rings, thus confirming the presence of a fine-grain structure. Coatings exhibit a hardness of 12 to 30 GPa.

What is claimed is:

1. An orthopedic prosthesis for implantation in a patient comprising
  at least one metallic component comprising
    a metallic substrate, and
    a protective coating integrally formed over said substrate, the coating and the substrate having at least one metallic constituent in common having an average atomic concentration in the coating that differs from an average atomic concentration in the substrate by less than about 20 percent, and said protective coating having a nanocrystalline structure with average grain sizes ranging from about 1 nanometer to about 999 nanometers, and a transition region extending from the coating to the substrate.

2. The orthopedic prosthesis of claim 1, wherein an average atomic concentration of said common metallic constituent in the coating differs from an average atomic concentration in the substrate by less than about 10 percent.

3. The orthopedic prosthesis of claim 1, wherein said common metallic constituent comprises cobalt having an average atomic concentration in a range of about 40 to about 75 percent.

4. The orthopedic prosthesis of claim 1, wherein said common metallic constituent comprises cobalt having an average atomic concentration in a range of about 45 to about 65 percent.

5. The orthopedic prosthesis of claim 1, wherein said common metallic constituent comprises cobalt having an average atomic concentration in a range of about 50 to about 60 percent.

6. The orthopedic prosthesis of claim 2, wherein said metallic substrate further comprises chromium (Cr) having an average atomic concentration in a range of about 30 to about 65 percent.

7. The orthopedic prosthesis of claim 2, wherein said metallic substrate further comprises chromium (Cr) having an average atomic concentration in a range of about 35 to about 55 percent.

8. The orthopedic prosthesis of claim 2, wherein said metallic substrate further comprises chromium (Cr) having an average atomic concentration in a range of about 40 to about 50 percent.

9. The orthopedic prosthesis of claim 6, wherein the coating further comprises chromium (Cr) having an average atomic concentration that differs from the average atomic concentration of chromium in the substrate by less than about 20 percent.

10. The orthopedic prosthesis of claim 6, wherein the coating further comprises chromium (Cr) having an average atomic concentration that differs from the average atomic concentration of chromium in the substrate by less than about 10 percent.

11. The orthopedic prosthesis of claim 3, wherein the metallic substrate further comprises molebdynum (Mo).

12. The orthopedic prosthesis of claim 1, wherein at least one of the substrate or the coating comprises a non-metallic substance having an atomic concentration less than about 20 percent.

13. The orthopedic prosthesis of claim 12, wherein said non-metallic substance is nitrogen.

14. The orthopedic prosthesis of claim 1, wherein the metallic substrate comprises a $Co_{57.1}Cr_{37.2}Mo_{5.7}$ alloy and the nano-crystalline coating comprises a $Co_{60.5}Cr_{39.5}$ alloy.

15. The orthopedic prosthesis of claim 1, wherein said common metallic constituent comprises titanium.

16. The orthopedic prosthesis of claim 9, wherein said substrate and said coating comprise a Ti-6Al-4V alloy.

17. The orthopedic prosthesis of claim 1, wherein the protective coating has a thickness ranging from about 0.05 microns to about a few millimeters.

18. The orthopedic prosthesis of claim 1, wherein the protective coating has a thickness ranging from about 0.05 microns to about 10 microns.

19. The orthopedic prosthesis of claim 1, wherein the protective coating has a thickness ranging from about 0.3 microns to about 3 microns.

20. The orthopedic prosthesis of claim 1, wherein an average grain size of the protective coating ranges from about 1 nanometer to about 500 nanometers.

21. The orthopedic prosthesis of claim 20, wherein an average grain size of the protective coating ranges from about 10 nanometers to about 200 nanometers.

22. The orthopedic prosthesis of claim 21, wherein an average grain size of the protective coating ranges from about 50 nanometers to about 200 nanometers.

23. The orthopedic prosthesis of claim 1, wherein the protective coating exhibits a greater hardness than the substrate.

24. The orthopedic device of claim 23, wherein the hardness of the protective coating is about 10% greater than that of the substrate.

25. The orthopedic prosthesis of claim 23, wherein the hardness of the protective coating is about 30% greater than that of the substrate.

26. The orthopedic prosthesis of claim 1, further comprising a plastic component articulating against the metallic component.

27. The orthopedic prosthesis of claim 26, wherein the plastic component is formed of ultra-high molecular weight polyethylene.

28. The orthopedic prosthesis of claim 26, wherein the prosthesis is an artificial hip.

29. The orthopedic prosthesis of claim 26, wherein the prosthesis is an artificial knee.

30. The orthopedic prosthesis of claim 26, wherein the prosthesis is an artificial shoulder.

31. An orthopedic prosthesis for implantation in a patient comprising
at least one metallic component comprising
a metallic substrate, and
a metallic protective coating integrally formed over said substrate, the coating and the substrate having at least one metallic constituent in common such that a concentration of said constituent in the coating differs from a concentration of said constituent in the substrate by less than about 20 percent, and said protective coating having a nanocrystalline structure with average grain sizes ranging from about 1 nanometers to about 999 nanometers, and
a transition region extending from the coating to the substrate.

32. The orthopedic prosthesis of claim 31, wherein an atomic concentration of said common metallic constituent in the coating differs from a concentration of said constituent in the substrate by less than about 10 percent.

33. The orthopedic prosthesis of claim 31, wherein said common metallic constituent comprises cobalt having an average atomic concentration in a range of about 40 to about 75 percent in said substrate.

34. The orthopedic prosthesis of claim 31, wherein said common metallic constituent comprises cobalt having an average atomic concentration in a range of about 45 to about 65 percent in said substrate.

35. The orthopedic prosthesis of claim 31, wherein said common metallic constituent comprises cobalt having an average atomic concentration in a range of about 50 to about 60 percent in said substrate.

36. The orthopedic prosthesis of claim 33, wherein said substrate and said coating include another common metallic constituent.

37. The orthopedic prosthesis of claim 36, wherein said another common metallic constituent comprises chromium having an average atomic concentration in a range of about 30 to about 65 percent in said substrate.

38. The orthopedic prosthesis of claim 36, wherein said another common metallic constituent comprises chromium having an average atomic concentration in a range of about 35 to about 55 percent in said substrate.

39. The orthopedic prosthesis of claim 36, wherein said another common metallic constituent comprises chromium having an average atomic concentration in a range of about 40 to about 50 percent in said substrate.

40. The orthopedic prosthesis of claim 37, wherein said chromium constituent has an average atomic concentration in said coating that differs from an average atomic concentration of chromium in the substrate by less than about 20 percent.

41. The orthopedic prosthesis of claim 37, wherein said chromium constituent has an average atomic concentration in said coating that differs from an average atomic concentration of chromium in the substrate by less than about 10 percent.

42. The orthopedic prosthesis of claim 31, wherein said substrate comprises a $Co_{57.1}Cr_{37.2}Mo_{5.7}$ alloy and the nanocrystalline coating comprises a $Co_{60.5}Cr_{39.5}$ alloy.

43. The orthopedic prosthesis of claim 31, wherein said common metallic constituent comprises titanium.

44. The orthopedic prosthesis of claim 43, wherein said substrate and said coating comprise a Ti-6Al-4V alloy.

45. The orthopedic prosthesis of claim 31, wherein the protective coating has a thickness ranging from about 0.05 microns to about a few millimeters.

46. The orthopedic prosthesis of claim 31, wherein the protective coating has a thickness ranging from about 0.05 microns to about 10 microns.

47. The orthopedic prosthesis of claim 31, wherein the protective coating has a thickness ranging from about 0.3 microns to about 3 microns.

48. The orthopedic prosthesis of claim 31, wherein an average grain size of the protective coating ranges from about 1 nanometer to about 500 nanometers.

49. The orthopedic prosthesis of claim 31, wherein an average grain size of the protective coating ranges from about 10 nanometers to about 200 nanometers.

50. The orthopedic prosthesis of claim 49, wherein an average grain size of the protective coating ranges from about 50 nanometers to about 200 nanometers.

51. The orthopedic prosthesis of claim 31, wherein the protective coating exhibits a greater hardness than the substrate.

52. The orthopedic device of claim 51, wherein the hardness of the protective coating is about 10% greater than that of the substrate.

53. The orthopedic prosthesis of claim 51, wherein the hardness of the protective coating is about 30% greater than that of the substrate.

54. The orthopedic prosthesis of claim 31, further comprising a plastic component articulating against the metallic component.

55. The orthopedic prosthesis of claim 54, wherein the plastic component is formed of ultra-high molecular weight polyethylene.

56. The orthopedic prosthesis of claim 54, wherein the prosthesis is an artificial hip.

57. The orthopedic prosthesis of claim 54, wherein the prosthesis is an artificial knee.

58. The orthopedic prosthesis of claim 54, wherein the prosthesis is an artificial shoulder.

59. The orthopedic prosthesis of claim 31, wherein the transition region exhibits a graded reduction in average grain size from the substrate to the coating.

* * * * *